United States Patent
Ronen et al.

(10) Patent No.: US 12,133,723 B2
(45) Date of Patent: *Nov. 5, 2024

(54) POSITION DETERMINATION SYSTEM AND METHOD

(71) Applicant: Medtronic Navigation, Inc., Louisville, CO (US)

(72) Inventors: Shai Ronen, Louisville, CO (US); Andrew Bzostek, Erie, CO (US); Brad Jacobsen, Erie, CO (US); Andrew Wald, Denver, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/900,010

(22) Filed: Aug. 31, 2022

(65) Prior Publication Data

US 2023/0000386 A1    Jan. 5, 2023

Related U.S. Application Data

(63) Continuation of application No. 15/963,444, filed on Apr. 26, 2018, now Pat. No. 11,439,317.

(51) Int. Cl.
| | |
|---|---|
| *A61B 5/06* | (2006.01) |
| *A61B 34/20* | (2016.01) |
| *G01R 33/02* | (2006.01) |
| *G01R 33/28* | (2006.01) |

(52) U.S. Cl.
CPC .............. *A61B 5/062* (2013.01); *A61B 34/20* (2016.02); *G01R 33/0206* (2013.01); *G01R 33/287* (2013.01); *A61B 2034/2046* (2016.02)

(58) Field of Classification Search
CPC . A61B 5/062; A61B 34/20; A61B 2034/2046; G01R 33/0206; G01R 33/287
See application file for complete search history.

(56) References Cited

U.S. PATENT DOCUMENTS

| | | | |
|---|---|---|---|
| 7,697,972 B2 | 4/2010 | Verard et al. | |
| RE44,305 E | 6/2013 | Foley et al. | |
| 8,644,907 B2 | 2/2014 | Hartmann et al. | |
| 8,842,893 B2 | 9/2014 | Teichman et al. | |
| 11,389,078 B2 * | 7/2022 | Govari | A61B 5/0538 |

(Continued)

FOREIGN PATENT DOCUMENTS

| | | | |
|---|---|---|---|
| EP | 1776923 A1 | 4/2007 | |
| EP | 1891895 A1 * | 2/2008 | A61B 34/20 |

OTHER PUBLICATIONS

Dos Santos Cassia Chapetti, "Nonlinear modeling of magnetic materials for electromagnetic devices simulation", 2017 IEEE XXIV International Conference Electronics (Year: 2017).*

(Continued)

*Primary Examiner* — Manuel A Rivera Vargas
(74) *Attorney, Agent, or Firm* — Harness, Dickey & Pierce, P.L.C.

(57) ABSTRACT

Disclosed is a method to remove distortion from a navigation system. The navigation system may be used to perform a procedure on a subject. The procedure may be any appropriate procedure. The navigation system may be used to account for the distortive effects of various conductive objects positioned near the subject on which the procedure is performed.

20 Claims, 4 Drawing Sheets

(56) References Cited

U.S. PATENT DOCUMENTS

2004/0199072 A1  10/2004  Sprouse et al.
2007/0244666 A1  10/2007  Li et al.

OTHER PUBLICATIONS

Dos Santos Cassia C Chapetti et al: "Nonlinear modeling of magnetic materials for electromagnetic devices simulation", 2017 IEEE XXIV International Conference Electronics, Electrical Engineering and Computing (Intercon), IEEE, Aug. 15, 2017 (Aug. 15, 2017), pp. 1-4, XP033232425, DOI: 10.1109/Intercon.2017.8079714 [retrieved on Oct. 20, 2017].
International Search Report and Written Opinion for Application No. PCT/US2019/029141 mailed Nov. 18, 2019.
European Patent Office, Communication Pursuant to Article 94(3), corresponding to European Application No. EP19732759.6, Dated Jul. 28, 2023 (3 pp).
U.S. Appl. No. 15/963,444, U.S. Pat. No. 11,439,317, filed Apr. 26, 2018, Shai Ronen et al.

* cited by examiner

POSITION DETERMINATION SYSTEM AND METHOD

CROSS REFERENCE

This application is a continuation of U.S. patent application Ser. No. 15/963,444 filed on Apr. 26, 2018. The entire disclosure(s) of (each of) the above application(s) is (are) incorporated herein by reference.

FIELD

The subject disclosure relates generally to a system and method for determining a position, including location and orientation, of a member in space based at least in part on a generated field.

BACKGROUND

This section provides background information related to the present disclosure which is not necessarily prior art.

In a navigation system for various procedures, such as surgical procedures, assembling procedures, and the like, an instrument or object may be tracked by measuring an effect of a magnetic field on a sensor coil. The sensor coil may include a conductive material that is placed within a magnetic field where a current is induced on the sensor coil. The measured induced current may be used to identify or determine a position of the instrument or object.

The electro-magnetic field may be generated with a plurality of coils, such as three orthogonally placed coils. Various transmitter or field generation systems include the AxiEM™ electro-magnetic navigation system sold by Medtronic Navigation, Inc., having a place of business in Louisville, Colorado The AxiEM™ electro-magnetic navigation system may include a plurality of coils that are used to generate an electro-magnetic field that is sensed by a tracking device, which may be the sensor coil, to allow a navigation system, such as a StealthStation® surgical navigation system, to be used to track and/or illustrate a tracked position of an instrument.

The navigation field volume is generally positioned near the patient so that it encompasses a region of the patient in which navigation would occur. Accordingly, the transmitter coil array may be near an individual, such as a surgeon, performing a procedure

SUMMARY

This section provides a general summary of the disclosure, and is not a comprehensive disclosure of its full scope or all of its features.

Disclosed is a transmitting assembly, particularly a transmitting coil array (TCA) that is configured and operable to transmit a diverse magnetic field. Particularly, the TCA is configured to generate field vectors that are diverse relative to one another for providing a relatively broad distribution of measurable orientations relative to an origin or within a volume. A sensor may be affected by a field component, such as a being affected by a flux of the generated field through the sensor (generally a coil of a conductive material) that induces a current within the conductive material. The induced current is measured to determine and/or measure flux of the field and is used to calculate a position of a tracking device. Generally more than one coil is affected by the field at a given position to allow for a determination of multiple degrees of freedom (e.g. location and orientation).

In various embodiments, a measurement of a flux through a coil, acting as the sensor, is equivalent to a measurement of the field component along a long axis of the coil. In various embodiments, sensors may measure other selected fields or field components. Correction due to distortion of fields, as disclosed herein, is applicable to any field measuring sensor. Herein reference to a flux measuring sensor is merely exemplary of a sensor for electro-magnetic navigation.

The TCA generates a field, the field may be a time varying magnetic field, that generates a flux through the tracking device. The flux of the field through the tracking device may vary depending upon the frequency of the transmitted field, the power of the transmitted field, and the distance of the TCA from the tracking device. The presence of certain materials at the vicinity of the TCA and/or the tracking device may affect the generated field and, therefore, the sensed field. A conductive item that is positioned within the field may give rise to eddy currents that will affect the field sensed by the tracking device. If items placed in the field affect or alter the flux of the field sensed by the tracking device, the calculated position of the tracking device may be inaccurate and lead to an inaccurate position determination. Therefore, disclosed are methods of removing or accounting for the effects due to an interference or distortion caused by conductive materials.

A calculation to account for the effects of distortion in a field may include determining a sensed flux or phase at a selected frequency. In various embodiments, the calculation to remove error may be to fit measured field effects such as flux and phase, to a model and extrapolate to a measured flux and phase at a zero frequency.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
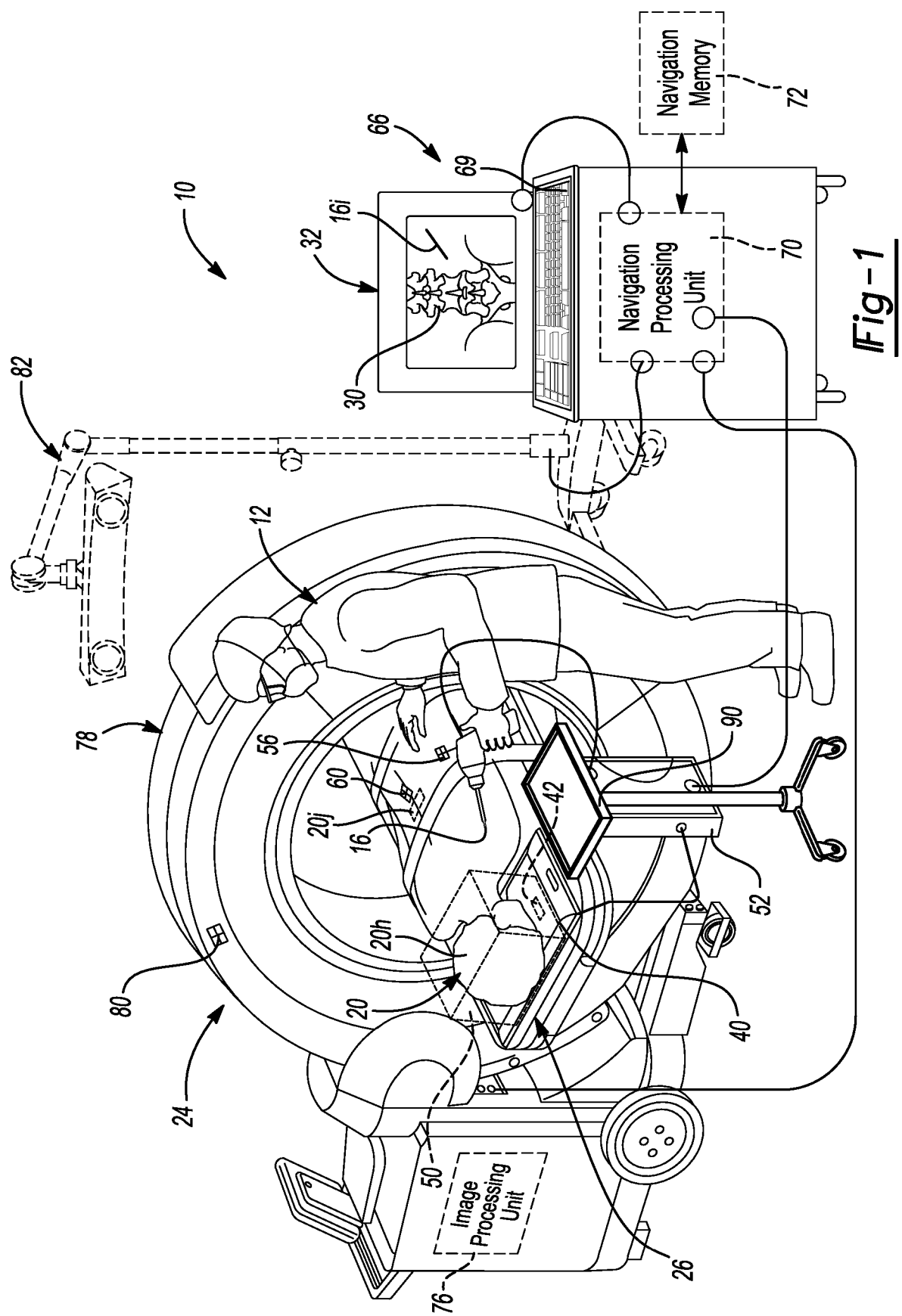
FIG. 1 is an environmental view of a navigation system.

With initial reference to FIG. 1, a navigation system 10 may be used for various purposes or procedures by one or more users, such as a user 12. The navigation system 10 may be used to determine or track a position of an instrument 16 in a volume. The position may include both a three dimensional X,Y,Z location and orientation. Orientation may include one or more degree of freedom, such as three degrees of freedom.

Tracking the position of the instrument 16 may assist the user 12 in determining a position of the instrument 16, even if the instrument 16 is not directly viewable by the user 12, or any external camera. Various procedures may block the visibility of instrument 16, such as performing a repair or assembling an inanimate system, such as a robotic system, assembling portions of an airframe or an automobile, or the like. Various other procedures may include a surgical procedure, such as performing low invasive, including a minimally invasive procedures including a spinal procedure, neurological procedure, positioning a deep brain simulation probe, or other surgical procedures on a living subject. In various embodiments, for example, the living subject may be a human subject 20 and the procedure may be performed on the human subject 20. It is understood, however, that the instrument 16 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 10, as discussed further herein, may incorporate various portions or systems, such as those disclosed in U.S. Pat. Nos. RE44,305; 7,697,972; 8,644,907; and 8,842,893; and U.S. Pat. App. Pub. Nos. 2004/0199072, all incorporated herein by reference. Various components that may be used with or as a component of the surgical navigation system 10 may include an imaging system 24 that is operable to image the subject 20, such as an O-Arm® imaging system, magnetic resonance imaging (MRI) system, computed tomography system, etc. A subject support 26 may be used to support or hold the subject 20 during imaging and/or during a procedure. The same or different supports may be used for different portions of a procedure. It is understood, however, that a selected operating theater need not include all of the portions discussed herein. Moreover, images may be acquired prior to a procedure or at any appropriate location and the imaging system 24 need not be present to acquire image data during a selected procedure.

Image data may be acquired during a surgical procedure or acquired prior to a surgical procedure for displaying an image 30 on a display device 32. The instrument 16 may be tracked in a trackable volume also referred to as a navigational volume through an EM field that is produced by a transmitter antenna or transmitting coil array that is incorporated into a localizer 40, as illustrated in FIG. 1. The position of the instrument 16 may be tracked in the tracking volume relative to the subject 20 and then illustrated as an icon 16i with the display device 32. In various embodiments, the icon 16i may be superimposed on the image 30 and/or adjacent to the image 30. As discussed herein, the navigation system 10 may incorporate the display device 30 and operate to render the image 30 from selected image data, display the image 30, determine the position of the instrument 16, determine the position of the icon 16i, etc.

With reference to FIG. 1, the localizer 40 may be an electromagnetic (EM) localizer that is operable to generate electro-magnetic fields with a transmitting coil array (TCA) 42 which is incorporated into the localizer 40. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electromagnetic fields generated will extend away from the coils 42 and form a navigation domain or volume 50, such as encompassing all or a portion of a head 20h, spinal vertebrae 20v, or other appropriate portion. The coils may be powered through a TCA controller and/or power supply 52.

The navigation domain or volume 50 generally defines a navigation space or patient space. As is generally understood in the art, the instrument 16, such as a drill, lead, etc., may be tracked in the navigation domain relative to a patient or subject with an instrument tracking device 56. For example, the instrument 16 may be freely moveable, such as by the user 12, relative to a dynamic preference frame (DRF) or reference frame tracker 60 that is fixed relative to the subject 20. Due to the tracking device 56 connected or associated with the instrument 16, relative to the DRF 60, the navigation system 10 may be used to determine the position of the instrument 16 relative to the DRF 60.

The tracking devices 56, 60 may include or be provided as selected sensors. The sensors may sense a selected portion or component of an EM field that is generated by the TCA 40. In various embodiments, the tracking sensors may include coils, such as a wire or thread of conductive material formed or placed in a coil. Such sensors may also be referred to as tracking or sensing coils (e.g.) that senses and are used to measure a magnetic field strength, component of a field, etc.

The navigation volume or patient space may be registered to an image space of the patient and the icon 16i representing the instrument 16 may be illustrated at a navigated (e.g. determined) and tracked position with the display device, such as superimposed on the image 30. Registration of the patient space to the image space and determining a position of a tracking device, such as with the tracking device 56, relative to a DRF, such as the DRF 60 may be performed as generally known in the art, including as disclosed in U.S. Pat. Nos. RE44,305; 7,697,972; 8,644,907; and 8,842,893; and U.S. Pat. App. Pub. Nos. 2004/0199072, all incorporated herein by reference.

The navigation system 10 may further include a navigation processor system 66. The navigation processor system 66 may include the display device 32, the TCA 40, the TCA controller 52, and other portions and/or connections thereto. For example, a wire connection may be provided between the TCA controller 52 and a navigation processing unit 70. Further, the navigation processor system 66 may have one or more user control inputs, such as a keyboard 69, and/or have additional inputs such as from communication with one or more memory systems 72, either integrated or via a communication system. The navigation processor system 66 may, according to various embodiments include those disclosed in U.S. Pat. Nos. RE44,305; 7,697,972; 8,644,907; and 8,842,893; and U.S. Pat. App. Pub. Nos. 2004/0199072, all incorporated herein by reference, or may also include the commercially available StealthStation® or Fusion™ surgical navigation systems sold by Medtronic Navigation, Inc. having a place of business in Louisville, CO.

Tracking information, including regarding the magnetic fields sensed with the tracking devices 56, 60, may be delivered via a communication system, such as the TCA controller, which also may be a tracking device controller 52, to the navigation processor system 66 including the navigation processor 70. Thus, the tracked position of the instrument 16 may be illustrated as the icon 16i relative to the image 30. Various other memory and processing systems may also be provided with and/or in communication with the processor system 66, including the memory system 72 that is in communication with the navigation processor 70 and/or an imaging processing unit 76. The image processing unit 76 may be incorporated into the imaging system 24, such as the O-Arm® imaging system, as discussed above. The imaging system 24 may, therefore, include various portions such as a source and a x-ray detector that are moveable within a gantry 78. The imaging system 24 may also be tracked with a tracking device 80. It is understood, however, that the imaging system 24 need not be present while tracking the tracking devices, including the instrument tracking device 56. Also, the imaging system 24 may be any appropriate imaging system including a MRI, CT, etc. In various embodiments, the localizer may also include an optical camera system 82. The optical camera system 82 may be used in conjunction with or alternatively to the TCA 40 for tracking the instrument 16.

Information from all of the tracking devices may be communicated to the navigation processor 70 for determining a position of the tracked portions relative to each other and/or for localizing the instrument 16 relative to the image 30. The imaging system 24 may be used to acquire image data to generate or produce the image 30 of the subject 20. It is understood, however, that other appropriate imaging systems may also be used. The TCA controller 52 may be used to operate and power the TCA 40, as discussed above.

The TCA 40 may be operated to transmit in a power range of about 0.01 milli-watts (mW) to about 30 watts (W), including about 0.1 mW to about 10 W, and further including about 0.1 mW to about 5 W. In various embodiments, the TCA controller 52 may operate at about 1 amp (A) to about 5 A, including about 1 A to about 3 A, and further including about 2 A. It is further understood, however, that the TCA 40 may be operated to transmit at any appropriate selected power and/or may be powered with a current greater than 2 A.

In various embodiments, however, the TCA 40 may be used to generate fields that are near various objects that may be conductive. In various embodiments the conductive objects may include all or a portion of the imaging system 24 (if present), the subject support 26, and/or other procedure instrumentation, such as a work or holding tray 90. As discussed herein, the various objects or elements may be referred to as interfering or disruptive members, objects, or elements. Generally, the interfering member may have a current induced therein that generates a field separate from those generated by the TCA 40. The tray 90 may be (or only one of) an interfering object, and is discussed herein as an example of an interfering object, and, therefore, the discussion of the tray 90 may relate to any appropriate object, unless specifically indicated otherwise. In other words, for the following discussion, the tray 90 may be referred to as an interfering member or tray for ease of the following discussion. It is understood, however, that various conductive members may be interfering members even if not specifically identified below. Further, though the following discussion is regarding an example including a single tray 90, more than one tray may be present and/or more than one interfering object may be present.

In operation the TCA 40, via the conductive coils 42, may generate a magnetic field into the navigation volume 50, as discussed above. The field generated by the TCA 40, however, may not be entirely encompassed within the navigation volume 50 and/or elements, such as the patient support 26, the work tray 90, or other items, may be positioned within the navigation volume 50 and/or interfere or be affected by the field generated with the TCA 40. When a conductive member, such as the tray 90, is affected by the field generated by the TCA 40, eddy currents may be produced in the tray 90. The tray 90, therefore, being affected by the field generated by the TCA 40, may generate eddy currents due to the effects of the generated field. The eddy currents may then form fields, such as magnetic fields, that are in addition to those produced by the TCA 40.

The fields produced by the tray 90 (interfering fields) may change, by superposition, the field generated by the TCA 40 alone.

In various embodiments, the field by the TCA 40 without the tray 90, or other interfering objects, may be referred to as a distortion free, clean, or pure field. The clean field may be calibrated, mapped, or otherwise determined (such as by measuring) to be known, such as having known field components or fluxes at known positions for navigation and tracking. These allow the clean field to be calibrated, as referred to herein. A representation of the calibrated field, such as the known components, may then be saved for later recall, such as from a memory system. In various embodiments the representation may include a look up table of known fluxes or field components and known positions relative to the TCA 40 may be generated and saved in the memory system 72. This look up table or information may be recalled during a procedure to compare to a measured flux or field strength to determine the current position of the tracking device 56 within the field and in the navigation space 50. It is further understood, however, that the field components may be any selected field components that are to be measured in the field and are not necessarily limited to flux. For example, a Hall effect sensor may be used to sense the field and the related undistorted sensed components may be included in the undistorted representation, such as the look-up table. As discussed herein, position of a tracked member or element, such as a sensor, may include a three dimensional (x, y, z) location alone and/or in combination with an orientation (including at least one of a yaw, pitch, or roll). Thus, position may refer to a selected degree of freedom, including at least six degrees of freedom, while position may include less degrees as well.

The TCA 40 in generating a field may cause eddy currents to be formed in various interfering materials such as the tray 90. The eddy currents may then generate additional magnetic fields that affect the field generated by the TCA 40, such as adding to or subtracting from the intended or original field. As the tracked position of the tracking devices, such as the tracking device 56, is based upon the sensed magnetic field altering the field generated by the TCA 40 may affect the determined or tracked position of the instrument 16.

In various embodiments, the field generated by the TCA 40 forms or defines the navigation volume 50, as illustrated in FIG. 1. The navigation volume 50 may then be analyzed or premeasured to determine the field strength, including magnetic flux and phase. The measurements of the field within the navigation domain 50 may then be stored in a selected database, such as a navigation volume database stored in the navigation memory 72, as discussed above. During a navigated procedure, the tracking device 56 may then sense the field in the navigation domain 50 and the position of the tracking device 56 may be determined with reference to the lookup table in the navigation memory 72. In particular, for example, the sensed or measured field in the navigation domain 50 may be compared to sensed or measured field strengths and/or phase in the lookup table recalled from the navigation memory 72. A position of the tracking device 56 may then be determined based upon a direct correlation to the lookup table and/or an interpolation between various measurements in the lookup table.

If the field generated by the TCA 40 is distorted in any manner, such as due to the work tray 90, the sensed field by the tracking device 56 within the navigation domain 50 may be altered from that pre-determined, measured, and saved during the calibration or setup phase. Accordingly, a distortion of the field within the navigation space 50 may alter the determined position of the tracking device 56. It may be determined to correct for any distortion that may occur in the field in the navigation space 50 to account for distortion and determine a correct and undistorted position of the tracking device 56. In various embodiments, correcting for the distortion may include determining a distortion free flux based on a modeled flux interpolated to zero frequency.

It is further understood that the position of the instrument 16 (e.g. a working end or patient interacting end) may be determined due to a predetermined position of the instrument 16 relative to the tracking device 56. For example, a predetermined geometric orientation and/or distance from the tracking device may be known, such as a tracked position of the tracking device 56, may be correlated to the instrument 16. Alternatively, or in addition thereto, a tracking device may be placed at the selected position of the instrument, such as a working or distal end of the instrument 16, to track a specific portion of the instrument 16.

Figure 2:
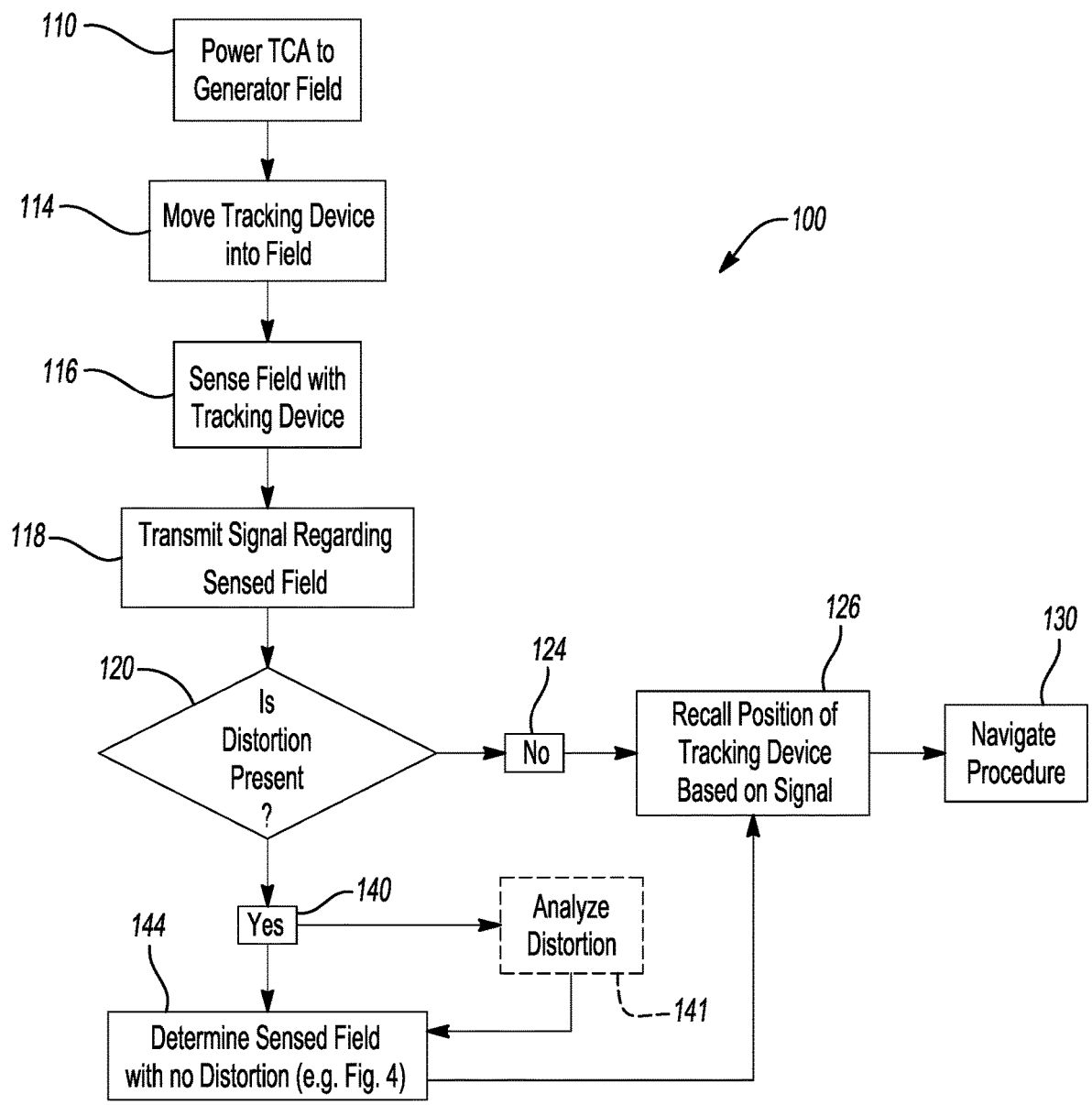
FIG. 2 is a flowchart of a process for navigating an instrument.

In various embodiments, with additional reference to FIG. 2, the navigation system 10 may generally operate as according to a flowchart 100. The TCA 40 is powered in block 110. In powering the TCA 40 in block 110, the field is generated by the TCA 40 to define the navigation space 50. A tracking device may then be moved into the field in block 114. It is understood that moving the tracking device into the field in block 114 may be performed in any appropriate manner such as movement by the user 12, movement by a robot, or movement under the instruction of the user 12. It is further understood that moving the tracking device into the field in block 114 is not a requirement, but is described for clarity of the current discussion. For example, the tracking device 56 may be positioned near the patient 20 such that the tracking device 56 is within the navigation volume 50 and, therefore, movement of the tracking device 56 in the navigation volume 50 is not required.

Nevertheless, the tracking device may then sense the field in block 116. After sensing the field 116, a signal may be transmitted to the navigation processor system 66 and/or the signal may be received by the navigation processor system 66 through an appropriate communication such as a wired, wireless, or other appropriate communication system. Further, as discussed above, the signal may be first transmitted to the TCA controller 52 and then relayed to the navigation processor system 66. Nevertheless, the signal may be transmitted to the navigation processor system 66. In various embodiments the signal may include a measurement or sensed field and the signal is based upon the sensed field in the navigation domain or volume 50.

A decision block 120 may then be entered to determine whether distortion is present in the field, such as within the navigation volume 50, based on the transmitted signal. A determination of whether distortion is present in the field may be based upon various evaluations, such as a type of distortion detected, a type of parameters of the signal received, or other appropriate determinations, as discussed further herein. In various embodiments, however, a determination that no distortion is present and a NO-path 124 may be followed.

If no distortion is determined to be present, the position of the tracking device 56 may then be determined based upon directly and with only the transmitted signal. As discussed above the navigation volume 50 may be calibrated at an appropriate time to determine positions and related sensed field strengths at the different positions. Accordingly, the determination of a position of the tracking device 56 may be based upon comparing the field strength transmitted in the signal to the lookup table, or other appropriate stored format of the field strengths, and recalling the related position. As is understood by one skilled in the art, the processor system 66 may also interpolate between calibrated positions in the look up table to determine the position of the tracking device 56.

The position may include both three-dimensional location and orientation in a selected number degrees of freedom (e.g. three degrees of freedom), thus, for example six degree of freedom position information may be determined. The position of the tracking device may, therefore, be recalled from the navigation memory 72 in block 126. Moreover, the position of the instrument 16 (or portion thereof, such as a terminal end) may be recalled and/or determined based upon the tracked and determined position of the tracking device 56 and the known position of the instrument 16 relative to the tracking device 56.

Once the position of the tracking device is recalled in block 126, a procedure may be navigated in block 130. Navigation of the procedure in block 130 may include various additional steps and/or procedures such as illustrating the icon 16*i* on the display device 32 relative to the image 30. As discussed above, the image space defined by the image 30 may be registered to the patient space, such as the navigation volume 50, through various registration techniques such as those discussed above and known by one skilled in the art. The user 12 may then view the position of the instrument 16 by viewing the icon 16*i* relative to the image 30 to assist in performing a procedure. Procedures may include various procedures such as manipulation and movement of an implant, removal of selected tissue, movement and placement of various assembly portions for inanimate or nonliving subjects, or the like. Nevertheless the procedure may be navigated in block 130 based upon a tracked position of the instrument 16 due to the tracking device 56.

In various embodiments, with continuing reference to FIG. 2, a distortion may be determined to be present from the decision block 120 and a YES-path through block 140 may be followed. Upon following the YES-path 140, it may be possible to analyze the type of distortion, prior to a determination of a sensed field with no distortion may be made in block 144. It is understood, however, that analyzing the distortion may not be required prior to the determination of the sensed field with no distortion made in block 144.

A determination of a sensed field with no distortion may be formed according to various techniques, including those discussed further herein. In various embodiments, for example, a determination of effects of magnetic fields not produced by the TCA 40 may be determined. A determination, according to the process discussed herein (i.e. Eq. 1), of a sensed magnetic field that is produced at a zero frequency transmission may be determined. The determination of the measured field at the zero frequency transmission may then be used to determine the undistorted or uninfluenced field that would be produced by the TCA 40 if an interfering object, such as the work tray 90, did not interfere with the field transmitted by the TCA 40.

Once the determination of a sensed field with no distortion is made in block 144, a recall of the position of the tracking device based on the signal is then be made in block 126. Once the signal of an undistorted field is determined in block 144, the saved or previously determined (i.e. calibrated) position of the tracking device 56 due to the sensed field is substantially the same as an undistorted or un-interfered with field, regardless of distortion in the navigation space 50. Accordingly, the distortion is effectively removed due to the determination of the sensed field with no distortion in block 144. Therefore, the removal of the distortion signal may be used to recall the determined position from the navigation memory 72 in block 126. The process 100 may then proceed and the selected procedure relative to the subject 20 may occur with navigation in block 130, as discussed above.

The flow chart 100 illustrates a process for allowing a navigation procedure to be navigated in block 130, even if distortion is present in a navigation field that defines or forms the navigation volume 50, as illustrated in FIG. 1. In particular, the operation of the navigation processing system 66, including the navigation processing unit 70, may operate efficiently and effectively to determine the position of tracked members, such as the tracking device 56, even in the navigation volume 50 that may have a distortion due to an interfering member, such as the work tray 90.

As noted above, in various embodiments, determining a sensed field with a no distortion in block 144 may allow for the navigation processing unit 70 to determine a true position of the tracking device 56 in the navigation volume 50. The true position of the tracking device 56 in the navigation volume 50 may be the position of the tracking device 56 in the volume 50 based upon the field generated by the TCA 40 with no interference in the field generated by the TCA 40, such as by the work tray 90. Generally, the tracking device 56 may sense the field generated by the TCA 40 in the navigation volume 50 and the position of the tracking device 56 may be determined by accessing the navigation memory 72. Application of various distortion removal techniques, however, may be used in determining a sensed field with no distortion block 144.

To correct for or remove distortion sensed in the field and incorporated in the signal from the respective tracking device, in various embodiments, the flux, from a field emitter such as the TCA 40, is measured at several frequencies greater than zero, and extrapolated to a non-distorted flux at zero frequency using a model described by equation 1

$$F_{(freq)} = F_0 + k_1 + j * \frac{k_1}{freq * \tau_1 - j} + k_2 + j * \frac{k_{12}}{freq * \tau_2 - j} \quad \text{(Eq. 1)}$$

$F_{freq}$ is the flux at a selected frequency and $F_0$ is a flux at zero frequency $k_1$, $k_2$, $f_{req}$, $\tau_1$, and $\tau_2$ are parameters that depend on the distorting material, its geometry, and location relative to the TCA 40 and sensor, and are to be determined continuously in real time by fitting the model to the measured $F_{freq}$. Eq. 1 may be incorporated or evaluated to model and assist in determining a zero frequency ($F_0$) at a tracking device, such as the tracking device 56, to assist in removing distortion of a distorting element or interfering member, such as the work tray 90. In addition, Eq. 1 may have additional additive terms of the form $$k_i + \frac{k_1}{freq * \tau_1 - j}. \quad \text{Eq. 2}$$

With reference to Eq. 1 and Eq. 2, included therein are various parameters that may be used to attempt to solve for the flux at a selected frequency ($F_{freq}$) wherein $F_0$ is a flux at zero frequency. The Eq. 1 is a model that may be used to simulate two or more circuits that are generated in the interfering member, such as the work tray 90, when eddy currents are formed therein due to the field emitted by the TCA 40. To attempt to determine the sensed field with no distortion in block 144, Eq. 1 is solved estimated for $F_0$.

In Eq. 1, F is the flux at the selected frequency and $F_0$ is the measured magnetic flux at a zero frequency. One skilled in the art will understand that at zero frequency there are substantially no eddy currents being generated in the interfering member, such as the work tray 90. Accordingly, modeling the sensed magnetic flux at a zero frequency would reduce or substantially eliminate any interference due to eddy currents formed in the work tray 90 when the eddy currents generate fields that may interfere with the pure or un-interfered field generated by the TCA 40 in the navigation volume 50 when no interfering object is present. As discussed above, the work tray 90 is an exemplary interfering member and any appropriate interfering member may be identified and accounted for or modeled according to the processes as discussed herein, and the discussion of the work tray 90 is merely exemplary and for ease of the current disclosure.

As noted above, the TCA 40 may generate a field from one or more of the coils 42 in the TCA 40. The coils 42 generate a signal at a plurality of frequencies. The tracking device 56 may include a selected number of receiving coils, such as three receiving coils. Each of the receiving coils may be referred to as coil 1, coil 2, and coil 3. The receiving coils may be positioned substantially orthogonally to one another and measure flux of a magnetic field through each of the selected coils (i.e. coil 1, coil 2, and coil 3) independently. The flux is generally measured within the navigation volume 50.

A signal regarding the magnitude and/or phase of the field may be transmitted to the navigation processing system 66 for determination of the position of the tracking device 56. The tracking device 56 may be similar to the tracking devices as disclosed in the patents incorporated by reference above and including in the tracking devices of the AxiEM™ tracking devices of the StealthStation Navigation Systems® sold by Medtronic, Inc. having a place of business in Colorado, USA.

In Eq. 1, the model may account for or attempt to model a selected number of circuits, such as two or more independent circuits, that may be RL (resistance—inductive) circuits. The two circuits may model the emitted fields based upon eddy currents formed in the work tray 90. Accordingly, in Eq. 1 the two or more circuits may be modeled and include parameters $\hat{\ }$ regarding the first circuit $\hat{\ }\hat{\ }\hat{\ }$ $\hat{\ }$ regarding the second circuit. Both circuits may be independent RL circuits. The parameter $\hat{\ }$ is the flux coupling of the first circuit and the parameter $\hat{\ }$ is the flux coupling of the second. In Eq. 1 $\hat{\ }\hat{\ }\hat{\ }\hat{\ }$ refers to the frequency that is measured, TA is a time corresponding to the decay of the first RL circuit, and $\hat{\ }$ is a time corresponding to the decay of the second RL circuit. The parameter $\hat{\ }$ refers to the imaginary components of the respective measured fields. Similar additional parameters apply if more RL circuits are used in the model.

Figure 3:
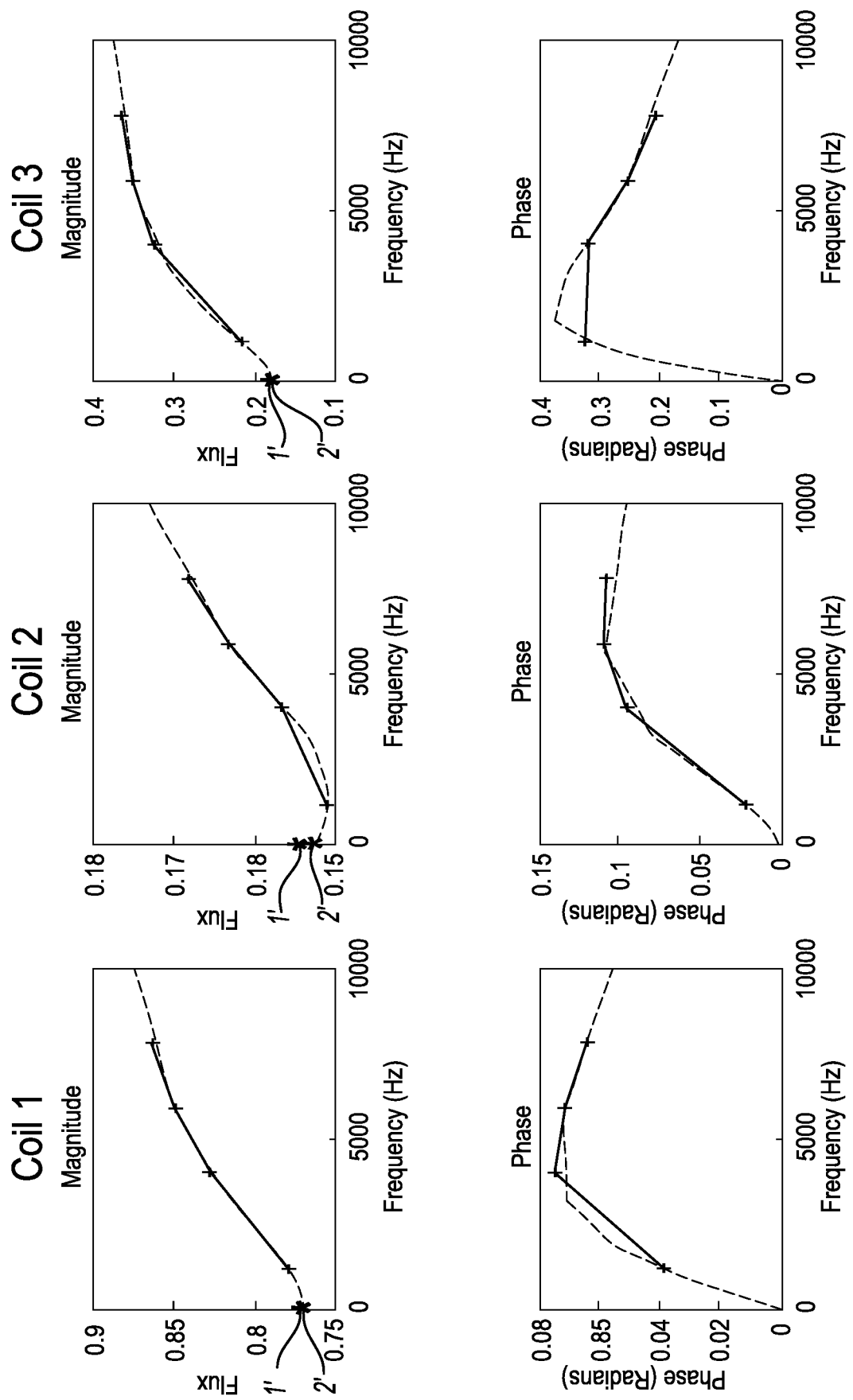
FIG. 3 is a graphical illustration of a model fitting process.

With reference to FIG. 3, the measured magnitude and phase of the field for three coils, such as three coils of the tracking device 56, are illustrated. It is understood that the phase and magnitude may refer to only the absolute values thereof. The tracking device 56 may also be referred to as a common tracker or tracking assembly (CTA). In various embodiments, as noted above, each of the three coils of the tracking device 56 may have a common origin. Each of the coils, however, may be positioned substantially orthogonally to one another around the common origin. The measured flux, including magnitude and phase thereof, at each of the three coils of the tracking device 56 may be used to determine the position of the tracking device 56. Further, the TCA 40 may include a plurality of the coils 52 of the transmitter array and each of the coils may transmit a signal varying by time or frequency that may be measured by the tracking device 56.

Accordingly, with reference to FIG. 3, the tracking device 56, as noted above may include the coil 1, coil 2, and coil 3. Illustrated in FIG. 3 is a representation of the sensed flux for each of the coils (identified in separated columns). Coil 1 may measure a magnitude of flux at a selected number of frequencies, such as 4 frequencies, identified by the crosses in the graph. Similarly a phase of the field may be measured at the same 4 frequencies. It is understood that the 4 frequencies may be emitted simultaneously or substantially simultaneously (such as with a short period of time, including on the order or milli- or -micro-seconds) and measured by coil 1. Similarly coil 2 and coil 3 may also measure magnitude of flux and phase of flux of the field at the respective coils 2 and 3, as identified by the crosses in FIG. 3. The measurements may also be simultaneous or substantially simultaneous.

With continued reference to FIG. 3, the model including Eq. 1 may be used to identify a fit of the measured flux and the Eq. 1 may be used to extrapolate and determine or estimate a flux at a zero frequency and phase. As discussed above, it is understood that there would be substantially no distortion or interference at a zero frequency transmission, such as without the distortion from the work tray 90. The fit may be determined using a least squares fit of the Eq. 1 model to the measured flux and phase at the frequencies, noted above. As identified in the graphs in FIG. 3, the fit is identified as the dashed line in each of the respective plots or graphs. It is further understood, however, that the tracking device 56 may be any appropriate type of sensor, such as a Hall effect sensor. The selected sensor of the tracking device may sense a component of the field and transmit a signal based on the sensed component. The determination and/or compensation of distortion sensed in any field component may be compensated in a similar manner. Accordingly, measuring flux and/or extrapolating a flux at a zero frequency is merely exemplary.

The extrapolation of Eq. 1 may be used to solve or identify the flux zero frequency ($F_0$). The calculated magnitude of flux at the zero frequency may then be used to identify the true or undistorted position of the tracking device 56 in the navigation volume 50. As discussed above, the correspondence between non distorted fluxes and position may be predetermined or calibrated and stored in the navigation memory 72.

Further, the measured flux with no distortion (i.e. no interfering object within the field) was also made and identified for each of the coils in, for an example. As illustrated in FIG. 3, the illustrated star 1' is the measured magnitude of flux with no distortion present (i.e. when work tray 90 is not present). The star 2' is the extrapolated or calculated magnitude of flux at a frequency zero based upon the fit and extrapolation to a zero frequency by fitting Eq. 1 to the measured magnitude and/or phase of flux. Accordingly, as illustrated in FIG. 3, the determined magnitude of flux at a frequency zero substantially matches the actual measured magnitude of flux at a zero frequency (i.e. when no work tray 90 is present).

Accordingly, the Eq. 1 may be used to model the magnitude of flux of the field generated by the TCA 40 in the navigation volume 50 when the work tray 90 is not present, even if the work tray 90 is present or interfering with the field. Therefore, the undistorted field may be calculated or determined in block 144. This allows for a determination of the position of the tracking device 56 in the navigation domain 50, such as by a calculation with the navigation processor system 66, even though work tray 90 is present. It is further understood that other interfering objects may be positioned in the navigation volume 50 and/or affect a field in the navigation volume 50 and the Eq. 1 may be used to determine or eliminate distortion in the navigation volume 50 due to the interfering objects. Accordingly, the processor system 66 may be operated in an efficient manner in light of the model including Eq. 1 to determine a position of the tracking device 56 even though an interfering object, such as the work tray 90, affects the field in the navigation volume 50. By accounting for or removing the distortion in the measured field, a true and undistorted position of the tracking device 56 may be determined.

As noted above, the position of the instrument 16 may be determined based upon the tracked position of the tracking device 56. This further allows for an identification and determination of the instrument relative to the patient 20 and the image 30 of the patient 20. Therefore, the display device 32 may illustrate or display the icon 16i that is rendered by the navigation system 66 on the display device 32 relative to the image 30. The procedure may therefore be navigated in block 130, as illustrated in FIG. 2.

Figure 4:
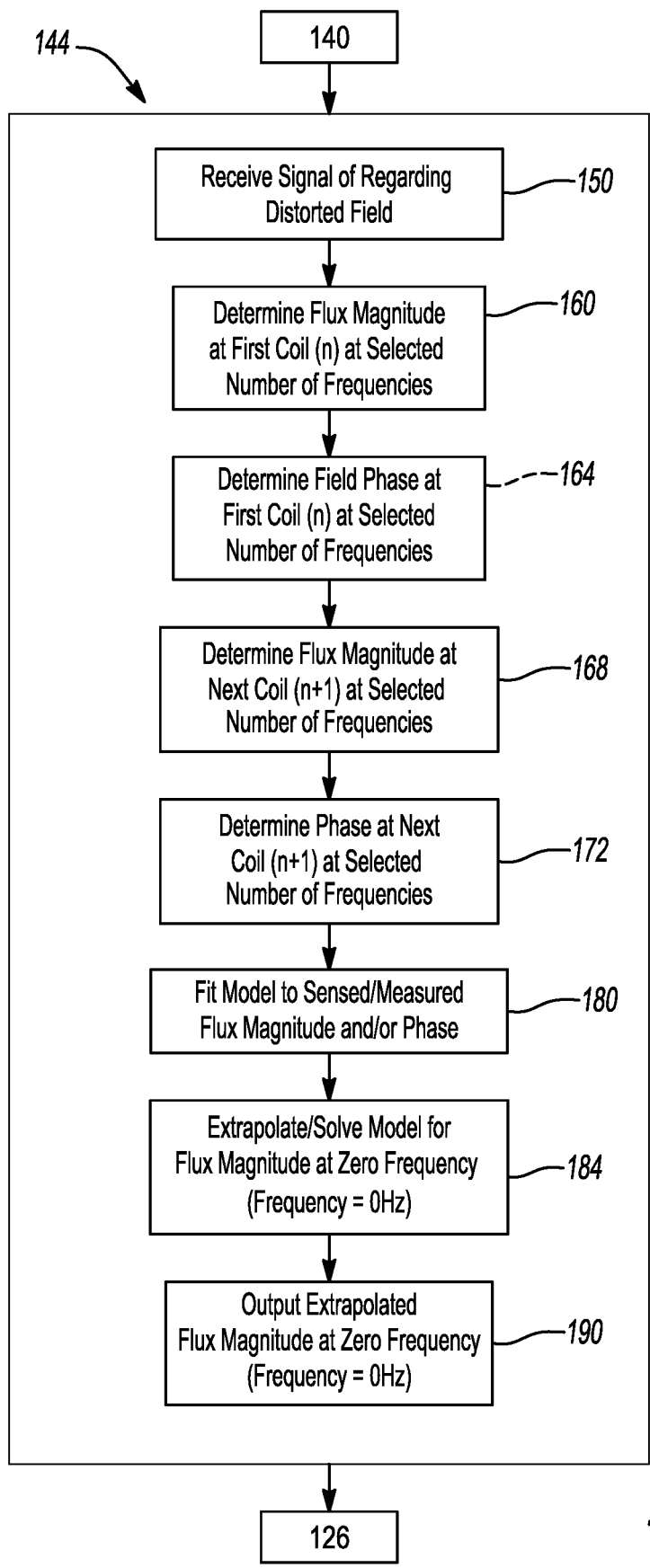
FIG. 4 is a flowchart of a process for removing distortion in a signal of a sensed field.

Turning reference to FIG. 4, the process 100 includes the block of determined sensed field with no distortion 144. According to various embodiments, determining a sensed field with no distortion may include removing the effect of distortion from the signal based on the sensed field (e.g. flux or phase). Removing the distortion in a signal regarding the sensed field may include fitting the signal to a selected model. As discussed above the model may include solving Eq. 1 according to a selected process, as discussed further herein.

The block 144 may include various sub-steps or sub-routines, as discussed herein. The process in block 144 may be included, as a set of instructions, an algorithm for determining a correction in light of a distorted field. Accordingly, the method described in FIG. 4 may be understood to be a flow diagram for an algorithm for determining or correcting a signal that is based on or a result of sensing a distorted field. It is understood, however, that the determination of a sensed field with no distortion may include any appropriate means based on Eq. 1 for converting the input signal based upon sensing a field with distortion and outputting a signal accounting or moving of the distortion. Accordingly, according to various embodiments, the means for determining the sensed field with no distortion in block 144 may include the model of Eq. 1 that may model two (or more) transformers or L circuits Generally, the determination of the sensed field with no distortion in block 144, however, may include receiving a signal of the distorted field in block 150. Receiving the signal may include receiving a signal from a tracking device, such as the tracking device 56, associated with the instrument 16. The signal may be transmitted to any appropriate portion, such as directly to the navigation processing unit 70 and/or through the TCA controller 52. Nevertheless, the determining of a sensed field flux with no distortion may include instructions that are executed by the navigation processing unit 70 and therefore the signal may be transmitted to the navigation processing unit 70 and received in block 150.

Once the signal is received by the processing unit 70, a distortion removal or correction means may be applied. The distortion removal or correction means may include application or performance of a set of instructions by the processing unit 70. Further, or alternatively thereto, a hardware system or circuit (such as an application specific integrated circuit) may be provided to account or mimic the dual transformer calculation or model as discussed above in relation to Eq. 1. Accordingly a distortion correction means may include a set of instructions executed by the processing unit 70 either alone or in combination with a hardware solution that corrects for the distortion according to the model of Eq. 1.

Nevertheless, the distortion correction is determined according to the method as illustrated in FIG. 4. Once the signal is received, a determination of a flux magnitude at a first coil at a selected number of frequencies is determined in block 160. As discussed above, the tracking device, such as the tracking device 56 may include one or a plurality of coils. As discussed herein, from the tracking device 56, therefore, a signal from a first coil is analyzed and signals from additional coils (i.e. n+1) coil until the signal from all or a selected number of the coils is analyzed. Each of the coils may sense the field to measure a magnitude of flux of the field through the coil. The magnitude of flux as measured by the coil is included in the signal received or transmitted regarding the sensed field in block 118. Accordingly, the determined flux magnitude of the first coil for a selected number of frequencies is made in block 160.

Further, as discussed above, the TCA 40 may generate one or a plurality number of frequencies with each of the coils. Each of the TCA coils 42 may generate the frequencies in a selected manner, such as substantially simultaneously and/or sequentially, such as in a time differential in series. In various embodiments, four frequencies may be generated by the TCA 40. Further, it is understood that the TCA 40 may include a plurality of conductive coils 42 therein. Each of the coils may generate fields at a selected frequency, including a selected number of frequencies, in a selected manner. Accordingly, determining a flux magnitude at a first coil at a selected number of frequencies may include determining a magnitude of flux at a plurality of frequencies.

With reference to FIG. 3, column 1 is the first coil (coil 1), column 2 is the second coil (coil 2), and column 3 is the third coil (coil 3). In the first row in FIG. 3 is a plot of measured flux of a field for a selected number of frequencies (i.e. four frequencies are illustrated in each plot) where crosses indicate the actual measured magnitude for each of the three coils at the different selected frequencies. Although four frequencies are measured and plotted, it is understood that any selected number of frequencies may be transmitted by the TCA 40 and measured by the tracking device 56. Moreover, it is understood that the frequencies may vary beyond those illustrated in the figures, such as lower than about 750 Hz or greater than about 8 kHz. The solid line connecting the crosses indicates a direct or straight line connection between the measured flux at the closest frequencies as plotted regarding the respective coils. The design and configuration of the coils 1, 2, and 3 in the tracking device 56 may be configured as discussed above.

The phase of the field sensed by each of the coils of the tracking device 56 may also be determined in a determined field phase at first coil at a selected number of frequencies in block 164. Again, with reference to FIG. 3, the second row illustrates the measured phase of the field at each of four selected frequencies at each of the three coils of the tracking device 56. Again the crosses indicate the actual measured phase of the field at the different frequencies, as plotted in the respective graphs. The solid line connects the measured phase at the closest frequencies. The frequencies are identical or substantially to the frequencies for the selected flux magnitude as illustrated in the first row in FIG. 3. It is also understood, that a different number or different range of frequencies may be transmitted by the TCA 40 and the phase measured at the selected coils relating to the selected frequencies.

Accordingly, a determination of a flux magnitude and a flux frequency phase for a selected number of frequencies may be determined for a first coil, such as the first column in FIG. 3. It is understood, as noted above, that a plurality of coils may be included in the tracking device 56. For example, as illustrated in FIG. 3, second and third coils may also be included in the tracking device 56. Accordingly, in blocks 168 and 172, respectively, a determination of a magnitude of flux at a selected additional number of coils, such as n+1 coils may be made and a determination of a phase of n+1 coils at the selected frequencies at block 172. Blocks 168 and 172, therefore, may be repeated for any selected number of coils. Accordingly, for example, as illustrated in FIG. 3, three coils may each have measured a magnitude of flux and a phase of flux for the selected number of frequencies, such as four frequencies. The measured magnitude and phase of flux may then be incorporated in the signal which is transmitted from the tracking device 56 and received into block 144. Accordingly, the determination of a magnitude of flux and a phase of flux for each of the three coils, or any selected number of coils is made in block 160-172, as illustrated in FIG. 4. Nevertheless, it is understood by one skilled in the art, that any appropriate number of coils and/or frequencies may be measured for fitting the model as described in Eq. 1.

Once a determination of the magnitude of flux and/or phase regarding the transmitted frequencies from the TCA 40 are made in blocks 160172, a model fit may be determined in block 180. The model fit in block 180 may be fitting the model as described by Eq. 1 to the magnitude of flux and/or phase of flux for each of the coils of the tracking device 56. As illustrated in FIG. 3 the dash line illustrates the model fit to the measured magnitude and/or phase of flux.

As described above the Eq. 1 includes various parameters relating to each of the frequencies. The flux at each selected frequency is the sum of various factors including the flux at a zero frequency, the parameter of flux coupling of a first RL circuit ($k_1$), and the flux coupling of a second RL circuit ($k_2$) plus a decay time for each of the respective circuits identified by $\tau$, where $T_1$ relates to the first RL circuit and $\tau_2$ relates to the second RL circuit along with imaginary components of the respective circuits identified by j. For four frequencies, therefore, the model is fit by selected fitting techniques, such as minimizing the square of errors, for each of the parameters $k_1$, $k_2$, $F_0$, $\tau_1$, and $\tau_2$. The parameters may be estimated or determined using the selected fit, such a minimizing errors, to best fit the model to the measured magnitude of fluxes at the different frequencies (i.e. four frequencies in the disclosed example, it is understood that more or less frequencies and different frequencies may be used and/or that more or additional parameters or parameter sets may be used to model additional RL circuits).

Once the model is best fit, $F_0$ may be estimated or extrapolated to calculate a flux at a zero frequency. The flux at a zero frequency is estimated to be the flux with no distortion due to the tray 90. Again, although the above disclosure exemplarily refers to the single tray 90, more than one interfering object may be present. The model, including Eq. 1, however, may still solve for the distortion as the effects are cumulative. The Eq. 1, therefore, may be used in a model to determine the flux in the navigation volume 50 regardless of the number of interfering objects. The extrapolation or solving of the model to a flux at a zero frequency is performed in block 184 and is done after fitting the model, such as estimating the parameters to a best fit, in block 180.

After extrapolating the model to a flux at a zero frequency an output of the magnitude of the flux at the zero frequency may be made in block 190. The output of the magnitude of flux at a zero frequency, as noted above, is determined to be the distortion free magnitude of flux measured at the tracking device 56. Accordingly, by extrapolating the model to the zero frequency flux a determination of a distortion free field may be made and output into block 190. In other words, correcting for the distortion may include determining a distortion free flux based on a modeled flux interpolated to zero frequency. The output in block 190 may then be used to recall the position of the tracking device in block 126, as illustrated in FIG. 2.

Further, the representation of the calibrated field that may be included as the predetermined table or calibration table may be made for a distortion free field generated by the TCA 40. Extrapolation or matching of a measured magnitude of flux may be matched to the table recalled in block 126 to make a determination or estimation of the position of the tracking device 56. By removing the distortion in block 144 and outputting the extrapolated zero frequency flux in block 190, the distortion free magnitude of flux determination may be used to recall the position of the tracking device in block 126. The procedure, therefore, may be navigated as if the tray 90 were not present to cause distortion in the field transmitted by the TCA 40. Accordingly the tracking or navigation volume 50 may be navigated in regardless of the presence of the tray 90 or not.

In various embodiments, the fit of the model, such as based on Eq. 1, may be used as a quality control and/or warning system. If the fit is not appropriate, such as within a selected threshold the user 12 may be warned (such as with a display with the display device (e.g. STOP) or a sound). A warning may also include discontinuing of the navigation, such as the display device becoming blank. Thus, the user 12 may be made aware that the fit of the model may not reach a selected threshold. Thus, the user 12 may alter the procedure, such as altering the work space near the navigation volume.

A threshold may include fit errors that are calculated (e.g. a sum of squared errors) between the model and the expected or known values that are greater than a selected amount. The fit errors, therefore, are generally selected to be small. If the amount is greater than a selected amount, then a sum of errors greater than a threshold may exist.

Generally, the errors that would lead to a bad fit of the model to the expected values may relate to an error or inaccurate navigated position. When an inaccurate navigated positon is determined, navigation may be halted and or a warning to the user 12 may be given. In various embodiments, the warning may be audio, visual, or some other appropriate warning or output to the user 12.

Also, as discussed above, the model fit need not be limited to measuring flux at a selected frequency and extrapolating flux at a zero frequency. Other selected field components may be measured and or effects, such as with a Hall effect sensor, at the tracking device. The sensor, of any appropriate type, may generate a signal based on the sensed field effect or component. The signal may be received and the model may be evaluated with selected parameters, such as based on a first, second or more circuits (such as R-L circuits). The model may be extrapolated to estimate the field component at a zero frequency and the estimation may be output. It is further understood that more than one field component may be included and/or measured. Thus, an undistorted field need not be determined based on or solely on an extrapolated flux at a zero frequency Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to track a member in a volume, comprising:
a transmitter operable to generate an electro-magnetic field at a plurality of frequencies;
a tracking device having at least a first sensor configured to sense the field at each frequency of the plurality of frequencies;
a processor system configured to:
receive a signal regarding the sensed field at the plurality of frequencies,
evaluate the received signal to determine if an interference is present,
if an interference is determined to be present, determine a distortion free flux based on a modeled flux interpolated to zero frequency, and
determine a position of the tracking device based on a distortion free field based on the determined distortion free flux.

2. The system of claim 1, further comprising:
a memory system having stored therein a representation of a distortion free field or one or more components of the distortion free field in a navigation volume;
wherein the processor system is configured to access the memory system to recall a position and/or orientation corresponding to the distortion free field.

3. The system of claim 2, further comprising:
an instrument associated with the tracking device, wherein the instrument includes a working end at a fixed geometry relative to the tracking device.

4. The system of claim 3, wherein the fixed geometry is determined and stored in the memory system.

5. The system of claim 1, wherein the tracking device further includes at least a second sensor and a third sensor;
wherein the signal includes information from each of the first sensor, the second sensor, and the third sensor regarding the field.

6. The system of claim 5, wherein the information regarding the field includes a magnitude of flux sensed at least at one of the first sensor, the second sensor, or the third sensor.

7. The system of claim 5, wherein the information regarding the field includes a phase as sensed at least at one of the first sensor, the second sensor, or the third sensor.

8. The system of claim 5, wherein the information regarding the field includes a magnitude of flux and a phase sensed at all of the first sensor, the second sensor, or the third sensor.

9. The system of claim 1:
wherein the modeled flux is based upon a model of two or more resistor-inductor (R-L) circuits.

10. The system of claim 1,
wherein the distortion free flux includes substantially no conductive interference from eddy currents in an interfering object.

11. A method of tracking a member in a volume, comprising:
receiving a signal from a sensor regarding at least one field component of a field in a navigation volume;
operating a processor system to:
evaluate a model including a first circuit parameter and a second circuit parameter,
determine a distortion free flux based on a modeled flux interpolated to zero frequency using the evaluated model, and
determine a position of the tracking device based on the distortion free flux at the zero frequency.

12. The system of claim 11, wherein evaluate a model including the first circuit parameter and the second circuit parameter, includes:
further operating the processor to recall from a memory system a set of instructions to:
evaluate a measured magnetic field flux at a first frequency as a model of a first resistor-inductor (R-L) circuit;
evaluate the measured magnetic field flux at the first frequency as a model of a second resistor-inductor (R-L) circuit.

13. The method of claim 12, further comprising:
further operating the processor system to execute instructions to sum the evaluations;
wherein the modeled flux is based on the sum of the evaluations.

14. The method of claim 13, further comprising:
fitting the model to a sensed magnetic field flux in the signal regarding the transmitted field.

15. The method of claim 11, further comprising:
providing the sensor as at least one coil positioned in a navigation volume into which the field is projected.

16. The method of claim 15, further comprising:
operating a transmitter to transmit the field at a plurality of frequencies;
wherein the signal includes information regarding the sensed transmitted field in the navigation volume.

17. The method of claim 11, further comprising:
operating the processor system to evaluate the received signal to determine if an interference is present;
wherein the evaluation of the model occurs if an interference is determined to be present.

18. The method of claim 11, wherein determine a position of the tracking device includes further operating the processor system to:
recall from a memory system a known representation of the at least one field component of the field in the navigation volume stored thereon; and
compare the at least one field component at the zero frequency to the known representation of the at least one field component;
wherein the known representation of the at least one field component includes a plurality of the at least one field component values that relate to positions in the navigation volume.

19. The method of claim 11, further operating the processor system to:
determine a distortion free field based on the distortion free flux.

20. A method of tracking a member in a volume, comprising:
operating a transmitter to transmit an undistorted field at a plurality of frequencies;
allowing an interfering object to interfere with the undistorted field to form a distorted field;
receiving a signal from a sensor at a position in a navigation volume regarding the distorted field at the position in the navigation volume, wherein the signal includes information regarding the distorted field in the navigation volume;
operating a processor system to:
and
determine a distortion free flux based on a modeled flux interpolated to zero frequency;
determine the position of the tracking device based on the distortion free flux at the zero frequency; and
operating a display device to display the determined position.

* * * * *